United States Patent
Verma et al.

(10) Patent No.: US 7,608,719 B2
(45) Date of Patent: Oct. 27, 2009

(54) PROCESS FOR THE PRODUCTION OF HETEROAROMATIC NITRILES IMPROVED CATALYST THEREFOR AND A PROCESS FOR THE PRODUCTION OF SAID IMPROVED CATALYST

(75) Inventors: Pradeep K. Verma, Noida (IN); Ashutosh Agarwal, Noida (IN)

(73) Assignee: Jubilant Organosys Limited, Uttar Pradech (IN)

( * ) Notice: Subject to any disclaimer, the term of this patent is extended or adjusted under 35 U.S.C. 154(b) by 242 days.

(21) Appl. No.: 10/489,073

(22) PCT Filed: Feb. 15, 2002

(86) PCT No.: PCT/IN02/00026

§ 371 (c)(1), (2), (4) Date: Jul. 30, 2004

(87) PCT Pub. No.: WO03/022819

PCT Pub. Date: Mar. 20, 2003

(65) Prior Publication Data

US 2004/0254379 A1    Dec. 16, 2004

(30) Foreign Application Priority Data

Sep. 7, 2001    (IN) ............................. 936DEL2001

(51) Int. Cl.
  *C07D 213/57* (2006.01)
(52) U.S. Cl. ...................................................... 546/286
(58) Field of Classification Search ................... 546/286
  See application file for complete search history.

(56) References Cited

U.S. PATENT DOCUMENTS 3,927,007 A    12/1975  Lussling et al.
4,336,205 A    6/1982   Onishi et al.

FOREIGN PATENT DOCUMENTS

DE    24 35 344 A1   2/1975
EP    0 290 996 A1   11/1988

OTHER PUBLICATIONS

Kirk, Encyclopedia of chemical technolgoy, ed. Mark et al., , NY: John Wiley & Sons, 3rd ed., 1978, 2, pp. 218-244.*

* cited by examiner

*Primary Examiner*—Patricia L Morris
(74) *Attorney, Agent, or Firm*—Nixon & Vanderhye P.C.

(57) ABSTRACT

A process for preparation of heteroaromatic nitrile from the corresponding alkyl pyridine is disclosed. The process comprises contacting the alkyl pyridine with ammonia and an oxygen source in the presence of a catalyst comprising an active component comprising of oxide of vanadium and antimony and a promoter provided on a support.

17 Claims, No Drawings

US 7,608,719 B2

PROCESS FOR THE PRODUCTION OF HETEROAROMATIC NITRILES IMPROVED CATALYST THEREFOR AND A PROCESS FOR THE PRODUCTION OF SAID IMPROVED CATALYST

FIELD OF THE INVENTION

The present invention relates to a process for the production of a heteroaromatic nitrile by ammoxidation of a corresponding alkyl-substituted pyridine. More particularly, the present invention relates to a process for the production of a heteroaromatic nitrile comprising reacting the corresponding alkyl-substituted pyridine with ammonia and molecular oxygen in gaseous phase over an improved catalyst. The present invention also relates to such improved catalyst for use in the production of heteroaromatic nitriles and to a process for the preparation thereof.

BACKGROUND OF THE INVENTION

Cyanopyridines have acquired tremendous importance in recent years since they form the starting materials for a number of valuable pharmaceutical intermediates and other commodities.

For catalyzing ammoxidation of an alkyl substituted heteroaromatic compound such as alkyl pyridines, several catalysts comprising vanadium oxides have been used. However, conventional catalysts possess very strong catalytic activity rendering them unsuitable for the ammoxidation of alkyl substituted pyridines. As a result of the strong catalytic activity of conventional catalysts, dealkylation or cleavage of the heteroaromatic ring occurs thereby resulting in low yields and low selectivity of the desired nitrites.

It is, therefore, important and essential to develop a catalyst for the ammoxidation of alkyl substituted heteroaromatic compound, which provides good yield and selectivity for the desired nitriles.

DISCUSSION OF PRIOR ART

Several processes are reported in the art for the catalytic ammoxidation of alkyl substituted heteroaromatic compounds to their corresponding nitrites. U.S. Pat. No. 2,510,605 discloses a catalyst containing vanadium, molybdenum and phosphorous with alumina as a carrier for the ammoxidation of picolines. Yields are reported to be approximately 60% at 450° C. The high reaction temperature in this reference is unsuitable from the industrial production point of view. European Patent No. 0253360 discloses vanadium, phosphorous and antimony oxides in combination as catalyst for the ammoxidation at a reaction temperature in the range of 420-430° C. Again, the high operating temperature is a serious limitation in terms of industrial operation. U.S. Pat. No. 5,910,465 discloses the ammoxidation of picolines over a multi-component catalyst comprising of vanadium, phosphorous, titanium or aluminium oxide with or without bismuth oxide. The catalyst is reduced at 450° C. before the reactants are passed over the catalyst.

U.S. Pat. No. 3,970,657 discloses the use of $V_2O_5+MoO_3+P_2O_5+MnSO_4$ with titanium dioxide. The conversion level of 3-picoline claimed in this disclosure is in the range of 52% and selectivity of up to 83%. The low conversion and selectivity levels render this process unattractive.

U.S. Pat. No. 2,839,535 discloses several $V_2O_3$ catalyst supported on $Al_2O_3$, heated at different temperatures and a process yield of 80% and 74% for isonicotinonitrile and nicotinonitrile respectively. U.S. Pat. No. 2,861,999 discloses similar yields for isonicotinonitrile and nicotinonitrile in the presence of large excess of air over a catalyst comprising oxides of vanadium, molybdenum and phosphorous supported on activated alumina. U.S. Pat. No. 5,658,844 discloses the use of vanadium antimony silica and titanium dioxide with one or more alkali metals.

European Patent No. 0037123 discloses a catalyst comprising vanadium, antimony and uranium or chromium oxides mixed with fine powder alumina. The catalyst needs a calcination temperature of 1300° C., rendering the process of catalyst preparation unattractive. The reference also recommends a very high mole ratio of air above 90 mole % per mole of beta picoline. This is also another disadvantage since it results in very high uncondensable gaseous effluent.

It is well known that transition metal oxides are good catalysts for selective oxidation and ammoxidation. A common characteristic of such oxides due to their ionic nature is the ability to transform bulk oxygen to the surface and later therefrom to the reactant molecules absorbed on it. The reduced catalyst is then rapidly reoxidised by molecular oxygen coming from the gas phase.

It is also important to consider here that ammoxidation reactions of alkyl-substituted heterocycles to produce corresponding heterocyclic aromatic nitriles are exothermic reactions. Thus, equilibrium conversion at low temperatures of exothermic reactions is desired.

OBJECTS OF THE INVENTION

It is, therefore, an object of the invention to provide a process for the production of heteroaromatic nitriles by the ammoxidation of corresponding alkyl-substituted pyridine derivatives, which ensures higher equilibrium conversion at lower temperatures of exothermic reactions to obtain better selectivities.

It is another object of the invention to provide a process for the production of heteroaromatic nitrites by the ammoxidation of the corresponding alkyl-substituted pyridine derivatives over an improved catalyst, which results in higher yield and selectivities.

It is a further object of the invention to provide an improved catalyst for the ammoxidation of alkyl-substituted pyridine derivatives to corresponding heteroaromatic nitriles which provides better yields and selectivities.

It is also an object of the present invention to provide a process for the preparation of an improved catalyst for use in the ammoxidation of alkyl-substituted pyridine derivatives to corresponding hetero aromatic nitriles

SUMMARY OF THE INVENTION

After extensive study and analysis, the applicants have found that in the preparation of cyanopyridines by the ammoxidation of alkyl pyridines, the abnormal reactions can be suppressed and nitrites obtained in good yield and selectivity when the catalyst of the present invention is used in the presence of a carefully selected promoter. In such reaction, the molar ratio of molecular oxygen and ammonia is also important. The catalyst of the invention comprises oxides of vanadium and antimony. The catalyst of the invention also has a good resistance to heat and reduction and is sage in operation.

Accordingly, the present invention provides a process for the preparation of a heteroaromatic nitrile from the corresponding alkyl pyridine which comprises contacting the alkyl pyridine with ammonia and an oxygen source in the presence of a catalyst comprising an active component consisting of oxides of vanadium and antimony and at least one promoter selected from chromium, molybdenum, cobalt and manganese oxides and any mixture thereof provided on a support.

In one embodiment of the invention, the oxygen source comprises air.

In another embodiment of the invention the promoter is selected from any one of chromium, molybdenum, cobalt and manganese oxides and any mixture thereof. In another embodiment of the invention, the catalyst is provided in the form of a catalyst bed.

In a further embodiment of the invention, the catalyst bed temperature is in the range of 300 to 390° C.

In another embodiment of the invention, the alkyl pyridine is in the form of vapors when contacted with the catalyst.

In another embodiment of the invention, the molar ratio of the alkyl pyridine to ammonia is in the range of 1:1 to 15, preferably 1:2 to 8, and most preferably 1:2 to 6.

In another embodiment of the invention, the molar ratio of the alkyl pyridine to air is in the range of 1:10 to 80, preferably 1:20 to 70, and most preferably 1:20 to 65.

In a further embodiment of the invention, the alkyl pyridine selected is 2-methyl pyridine to obtain 2-cyanopyridine (2-pyridine nitrile).

In a further embodiment of the invention, the alkyl pyridine selected is 3-methyl pyridine to obtain 3-cyanopyridine (3-pyridine nitrile).

In a further embodiment of the invention, the alkyl pyridine selected is 4-methyl pyridine to obtain 4-cyanopyridine (4-pyridine nitrile).

In yet another embodiment of the invention, the alkyl pyridine starting material comprises a mixture of picolines to obtain a mixture of nitrites.

In a further embodiment of the invention, the alkyl pyridine comprises lutidine to obtain mono or di nitrile.

The present invention also provides an improved catalyst for the production of heteroaromatic nitrites from the corresponding alkyl-substituted pyridine derivatives, comprising an active component consisting of oxides of vanadium and antimony and a promoter in the molar ratio of vanadium: antimony:promoter=1:0.1 to 1.0:0.1 to 0.51:0.1 to 1.0:0.1 to 0.5, said active component being supported on a low surface area catalyst support material.

In one embodiment of the invention, the promoter is selected from at least one of chromium, molybdenum, cobalt and manganese oxides and any mixture thereof. In another embodiment of the invention, the catalyst support material comprises alpha alumina of surface area less than 10 sq.m/gm.

The present invention also relates to a process for the preparation of an improved catalyst for the production of heteroaromatic nitriles from the corresponding alkyl-substituted pyridine derivatives, said process comprising:

(a) preparing a solution of a vanadium source in water;
(b) adding a weak organic acid to the solution obtained in step (a) above and mixing the solution obtained thoroughly;
(c) adding antimony oxide and promoter oxide to the solution obtained in step (b) above and heating the solution to obtain a slurry;
(d) adding a catalyst support material having a low surface area in the solid state in the required shape and size and mixing till a final coated mass is obtained;
(e) drying the mass of step (d) above and calcining the dried mass at a temperature in the range of 400-600° C.

In a preferred embodiment, the molar ratio of said weak organic acid to the solution of vanadium source is in the in the range from 1:1 to 4 by weight.

In another preferred embodiment, the solution in step (c) is heated to a temperature in the range of 60-90° C. to obtain said slurry.

In another embodiment, the weight ratio of vanadium: antimony:promoter in step (c) is 1:0.1 to 1.0:0.1 to 0.5

In another embodiment of the invention, the catalyst support material comprises alpha alumina of surface area less than 10 sq.m/gm.

In another embodiment of the invention, the vanadium source is selected from vanadium pentoxide and ammonium metavanadate.

In yet another embodiment of the invention, the antimony oxide comprises trivalent form thereof.

In another embodiment of the invention, the promoter comprises at least one of chromium, molybdenum, cobalt and manganese oxides and any mixture thereof.

In another embodiment of the invention, the active component is repeatedly coated on the catalyst support.

In a further embodiment of the invention, the loading of the active material on the catalyst support is in the range of 5 to 25%, preferably 5 to 15%.

In yet another embodiment of the invention, the ratio of vanadium is higher than that of the antimony and the promoter.

DETAILED DESCRIPTION OF THE INVENTION

When a molar ratio of molecular oxygen and ammonia is used and a vanadium antimony oxide and a promoter as described herein is used in the preparation of cyanopyridines by the ammoxidation of alkyl pyridines, abnormal reactions are suppressed and nitriles obtained in good yield and selectivity. The catalyst of the invention also has a good resistance to heat and reduction and is safe in operation.

The process of the invention for the production of cyanopyridine comprises contacting the corresponding alkyl pyridine with a catalyst bed of vanadium oxide, antimony oxide (trivalent form) and any one or more of chromium, molybdenum, cobalt and manganese oxides as promoter. The catalyst bed temperature is maintained in the range of 300 to 390° C. The alkyl pyridine is preferably in the form of vapors when contacted with the catalyst bed.

The molar ratio of the alkyl pyridine to ammonia is in the range of 1:1 to 15, preferably 1:2 to 8, and most preferably 1:2 to 6. The molar ratio of the alkyl pyridine to air is in the range of 1:10 to 80, preferably 1:20 to 70, and most preferably 1:20 to 65. It is advisable that the ratio of vanadium be slightly higher than that of the antimony component and the promoter component in the catalyst.

The alkyl pyridines used may be any pyridine derivatives such as 2-methylpyridine, 3-methylpyridine, 4-methylpyridine, mixture of picolines and lutidine to obtain 2-cyanopyridine or 2-pyridine nitrile, 3-cyanopyridine or 3-pyridine nitrile, 4-cyanopyridine or 4-pyridine nitrile, mixture of nitrites and mono or di nitrile respectively.

The catalyst of the invention comprises vanadium oxide, antimony oxide and a promoter oxide wherein the molar ratio of vanadium:antimony:promoter is 1:0.1 to 1.0:0.1 to 0.5, said oxides being supported on a low surface area catalyst support material. The promoter oxide is selected from at least one of chromium, molybdenum, cobalt and manganese oxides. The catalyst support material, preferably, comprises alpha alumina of surface area less than 10 sq.m/gm.

The catalyst of the invention is prepared by (a) preparing a solution of vanadium salt in water;
(b) adding a weak organic acid to the said solution obtained in step (a)
(c) mixing the solution obtained in step (b) above thoroughly;
(d) adding antimony oxide and promoter oxide in the weight ratio of vanadium:antimony:promoter=1:0.1–1.0:0.1–0.5;
(e) heating the mixture slurry of step (d) above to 60-70° C.;
(f) adding a catalyst support material having a low surface area in the solid state in the required shape and size and mixing till a final coated mass is obtained;
(g) drying the mass of step (f) above and calcining the dried mass at a temperature in the range of 400 to 600° C.

The active component may be repeatedly coated on the catalyst support to obtain the desired percentage of loading. The loading of the active material on the catalyst support should preferably be in the range of 5 to 25%, more preferably 5 to 15%.

Preferably, the ratio of said vanadium salt solution to said weak acid from 1:1 to 4 by weight. Preferably, the acid is oxalic acid.

The following examples are illustrative of the invention and should not be construed as limiting the scope of the invention in any manner. It is understood that variations of the processes described below are possible without departing from the scope and spirit of the invention.

Preparation Of Catalyst

EXAMPLE 1

Oxalic acid 1.0 kg was taken in 6 ltr. DM Water in an SS vessel with a mechanical stirrer. Vanadium pentoxide 500 gms. were added under stirring. Heating was slowly started at 70-80° C. Antimony oxide 300 gms. were added followed by chromium 150 gms. The mixture was heated to 90-80° C. to concentrate the solution till thick slurry was obtained. The support 5.0 kg. in the form of 3-4 mm pellets were added to the above slurry under constant agitation and heating was continued. The coated thick mass obtained was carefully dried at 150-170° C. The dried mass was then slowly calcined in a muffle furnace at 450-500° C. for 5 hours. The calcined mass was sieved to remove the powder and loosely held ingredients. The final preparation was examined and analysed to determine the amount of active material present on the support. If desired, repeated coatings can be carried out to ensure necessary percentage loading on the support material of the active ingredients. The coated mass thus obtained is between 10-20% by weight of the support. For the best results, the active material over the carrier should be between 3-35% preferably between 8-25% by weight.

EXAMPLE 2

The same procedure as in Example 1 was followed except that ammonium metavanadate was used in instead of vanadium pentoxide. Calcination was carried out at 500-525° C. and the active component over the support was 15%.

EXAMPLE 3

Example 2 was repeated using high fired silica/alumina of very low surface area and the active component coating obtained was approximately 16.5%.

EXAMPLE 4

Example 1 was repeated where vanadium, antimony and the third component ratio was maintained at the level of 1:0.8:0.15 respectively. The catalyst was calcined at 600° C. and the coating obtained was 12%.

The catalysts prepared in the above-mentioned examples were individually used in the preparation of cyanopyridines from methylpyridines and satisfactory results were obtained.

The following procedure was adopted for evaluating the catalyst and optimizing the process parameters. The alkyl pyridines were vaporized at 275-425° C. in a preheater and the superheated vapors were allowed to pass over a catalyst bed maintained at a temperature in the range of 350-425° C. Ammonia and air are allowed to enter and mix with the picolines above the catalyst bed.

The reaction is carried out in a stainless steel reactor with 1 meter length and 23 mm ID mounted in a vertical zone tubular furnace. Catalyst was diluted with inert and packed in the reactor. Above the catalyst bed, packing of inert material such as porcelain or glass beads were placed to ensure proper distribution of the reactants. The reactor tube is heated and the temperature is maintained as per the requirement. The feeder line is provided with three attachments, first for air, second for ammonia, and the third for the alkyl pyridines. The first zone of the reactor tube packed with inert acts as a vaporizer and super heater. Condenser traps and heater scrubbers are attached to the bottom outlet of the reactor in order to quench the product as soon as they exit the catalyst bed. Temperature of these condensers is maintained below 10° C. by the circulation of chilled brine.

The process of the invention for the preparation of heteroaromatic nitriles is illustrated below with reference to the following examples.

EXAMPLE 5

A run was carried out following the procedure described above and keeping the mole ratio of the reactants picoline:ammonia:air as 1:5:80 using the catalyst of Example 1. Results are provided in Table 1 below:

TABLE 1

| S. No. | Reactants | Product | Yield (%) | Conversion (%) |
|---|---|---|---|---|
| a. | 2-methyl pyridine | 2-cyanopyridine | 60 | 75 |
| b. | 3-methyl pyridine | 3-cyanopyridine | 80 | 89 |
| c. | 4-methyl pyridine | 4-cyanopyridine | 85 | 90 |

EXAMPLE 6

The same procedure as in Example 5 was followed except that the catalyst used was that obtained in Example 2. The results are provided in Table 2 below:

TABLE 2

| S. No. | Reactants | Product | Yield (%) | Conversion (%) |
|---|---|---|---|---|
| a. | 2-methyl pyridine | 2-cyanopyridine | 65 | 80 |
| b. | 3-methyl pyridine | 3-cyanopyridine | 85 | 92 |
| c. | 4-methyl pyridine | 4-cyanopyridine | 88 | 94 |

EXAMPLE 7

The catalyst used was that obtained in Example 4 and the molar ratios of the reactants was beta picoline:ammonia:air=1:2:80 and the effect of varying the percentage of coating over the inert carrier was studied. Results obtained are provided in Table 3 below:

TABLE 3

| S. No. | Percentage of active coating over carrier | Yield (%) | Conversion (%) |
|---|---|---|---|
| 1. | 5 | 48 | 65 |
| 2. | 10 | 68 | 80 |
| 3. | 20 | 86 | 94 |
| 4. | 25 | 84 | 98 |

EXAMPLE 8

Catalyst and conditions mentioned in example 6 above were scaled up to 5 times using beta picoline as reactant. The life of the catalyst in terms of commercial suitability was assessed. The results are provided in Table 4 below.

TABLE 4

| S. No. | Time on stream (hours) | Yield (%) | Conversion (%) |
|---|---|---|---|
| 1. | 12 | 80 | 92 |
| 2. | 24 | 83 | 93 |
| 3. | 48 | 85 | 90 |
| 4. | 60 | 85 | 91 |
| 5. | 100 | 85.5 | 92 |
| 6. | 200 | 86 | 92 |
| 7. | 300 | 86 | 92.5 |
| 8. | 400 | 86 | 91.5 |
| 9. | 500 | 86 | 92.0 |
| 10. | 600 | 86 | 91.5 |
| 11. | 700 | 86 | 92 |
| 12. | 800 | 86 | 92 |
| 13. | 900 | 86.5 | 92 |
| 14. | 1000 | 86 | 92 |

The catalyst performed exceptionally well and without any deviation in the activity for 1000 hours of continuous run. Based on the above, it is evident that the catalyst life of the catalyst of the invention is high and steady results are obtained at commercial level.

It was also observed in all the above experiments that the side products formed in the prior art due to the dealkylation of ring and ring destruction are suppressed and a high yield of cyanopyridines are obtained when the molar ratio of the alkyl pyridines, air and ammonia are maintained in a specific range and the improved catalyst of the invention is used.

We claim:

1. A process for the preparation of cyanopyridines from the corresponding alkyl pyridine comprising contacting the alkyl pyridine with ammonia and an oxygen source in the presence of a catalyst comprising said catalyst comprising an active component comprising an oxide of vanadium and antimony and a promoter selected from one or more of chromium, molybdenum, cobalt and manganese oxides and any mixture thereof, wherein the molar ratio of vanadium:antimony:promoter is in the range of 1:0.1 to 0.9:0.1 to 0.5, said active component being supported on a low surface area catalyst support material consisting of alpha alumina with surface area less than 10 sq.m/gm, wherein the ratio of ammonia to oxygen source is in the range of 2 to 8:10 to 80, and wherein the catalyst performs without deviation in activity up to 1000 hours of continuous run.

2. A process as claimed in claim 1 wherein said catalyst is provided in the form of a catalyst bed.

3. A process as claimed in claim 1 wherein the catalyst bed is at a temperature in the range of 300 to 390° C.

4. A process as claimed in claim 1 wherein the alkyl pyridine is contacted with the catalyst is in vapor form.

5. A process as claimed in claim 1 wherein the molar ratio of the alkyl pyridine to ammonia is in the range of 1:1 to 15.

6. A process as claimed in claim 5 wherein the molar ratio of the alkyl pyridine to ammonia is in the range of 1:2 to 8.

7. A process as claimed in claim 1 wherein the molar ratio of the alkyl pyridine to air is in the range of 1:10 to 80.

8. A process as claimed in claim 7 wherein the molar ratio of the alkyl pyridine to air is in the range of 1:20 to 70.

9. A process as claimed in claim 1 wherein the alkyl pyridine selected is 2-methyl pyridine to obtain 2-cyanopyridine.

10. A process as claimed in claim 1 wherein the alkyl pyridine selected is 3-methyl pyridine to obtain 3-cyanopyridine.

11. A process as claimed in claim 1 wherein the alkyl pyridine selected is 4-methyl pyridine to obtain 4-cyanopyridine.

12. A process as claimed in claim 1 wherein the alkyl pyridine starting material comprises a mixture of picolines to obtain a mixture of nitriles.

13. A process as claimed in claim 1 wherein the alkyl pyridine comprises lutidine to obtain mono or di nitrile.

14. A process as claimed in claim 1 wherein said catalyst support material comprises alpha alumina with surface area less than 10 sq.m/gm.

15. A process as claimed in claim 5, wherein the molar ratio of the alkyl pyridine to ammonia is in the range of 1:2 to 6.

16. A process as claimed in claim 7, wherein the molar ratio of the alkyl pyridine to air is in the range of 1:20 to 65.

17. A process for the preparation of cyanopyridines from the corresponding alkyl pyridine comprising contacting the alkyl pyridine with ammonia and air in the presence of a catalyst comprising said catalyst comprising an active component comprising an oxide of vanadium and antimony and a promoter selected from one or more of chromium, molybdenum, cobalt and manganese oxides and any mixture thereof, wherein the molar ratio of vanadium:antimony:promoter is in the range of 1:0.1 to less than 1.0:0.1 to 0.5, said active component being supported on a low surface area catalyst support material consisting of alpha alumina with surface area less than 10 sq.m/gm, wherein the ratio of ammonia to air is in the range of 2 to 8:10 to 80, and wherein the catalyst performs without deviation in activity up to 1000 hours of continuous run.

* * * * *